(12) United States Patent
Ulmsten et al.

(10) Patent No.: US 6,503,190 B1
(45) Date of Patent: Jan. 7, 2003

(54) VAGINAL PESSARY

(75) Inventors: Ulf Ivar Ulmsten, Danderyd (SE); Christer Sjogren, Viken (SE)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/677,101

(22) Filed: Sep. 29, 2000

(51) Int. Cl.$^7$ ................................................. A61F 2/00
(52) U.S. Cl. ............................ 600/29; 128/DIG. 25; 128/834
(58) Field of Search .................. 600/29, 30, 32; 128/DIG. 25, 885, 830, 834; 604/279, 515, 517

(56) References Cited

U.S. PATENT DOCUMENTS

| | | | | |
|---|---|---|---|---|
| 4,155,991 A | * | 5/1979 | Schopflin et al. | 424/15 |
| 4,307,716 A | * | 12/1981 | Davis | 128/834 |
| 5,188,835 A | | 2/1993 | Lindskog et al. | |
| 5,236,466 A | * | 8/1993 | Dumon | 128/830 |
| 5,611,768 A | * | 3/1997 | Tutrone, Jr. | 600/29 |
| 5,722,931 A | * | 3/1998 | Heaven | 600/29 |
| 5,771,899 A | * | 6/1998 | Martelly et al. | 128/834 |
| 6,056,687 A | | 5/2000 | Polyak et al. | |
| 6,086,909 A | * | 7/2000 | Harrison et al. | 424/430 |
| 6,090,098 A | | 7/2000 | Zunker et al. | |

FOREIGN PATENT DOCUMENTS

| | | |
|---|---|---|
| WO | WO 95/05790 | 3/1995 |
| WO | WO 98/42281 | 10/1998 |

* cited by examiner

Primary Examiner—John P. Lacyk

(57) ABSTRACT

A device for treating female incontinence and prolapse includes a vaginal insert. The insert may also be loaded with various pharmacological compounds/drugs, such as hormones for treatment of various diseases within or outside the urogenital tract. The insert has a generally cylindrical body dimensioned to allow insertion into the vagina. The body has a pair of spaced peripheral rings extending from the exterior surface of the body, which displaces the vaginal wall, the tissue between the vaginal wall and the urethra to apply pressure to the urethra to treat the various defects. The pessary may be split to allow coiling to aid in inserting the device.

23 Claims, 2 Drawing Sheets

VAGINAL PESSARY

FIELD OF THE INVENTION

The present invention relates to a vaginal device for therapeutic and diagnostic purposes, and more particularly to a resilient vaginal insert that exerts pressure upon the vaginal walls to diagnosis and treat various types of pelvic floor defects including urinary incontinence and prolapse and also to a system for the controlled and sustained delivery of pharmacological compounds for treatment of various diseases inside or outside the genital tract.

BACKGROUND OF THE INVENTION

A significant number of women suffer from urinary stress Incontinence, primarily as a consequence of stresses to the musculature of the pelvic floor and ligaments supporting the bladder associated with childbirth. Surgical remedies and apparatus are known, such as that disclosed in U.S. Pat. No. 5,899,909 relating to a method and apparatus for placing a supportive surgical tape beneath the urethra. Surgery is contraindicated in some patients, however, due to intolerance to anesthesia, preference or other reasons. In addition to surgical treatments for incontinence, it has been known for many years that a suitably proportioned object placed within the vagina proximate to the urethra and/or bladder can be used to support, reposition and/or constrict the urethra and/or bladder to ameliorate incontinence. For example, an inflatable toroidal bladder (U.S. Pat. No. 5,007,894) and a five-sided plate with a U-shaped indentation for supporting/occluding the urethra (U.S. Pat. No. 4,139,006) have been proposed for vaginal insertion to treat incontinence. Certain of the proposed vaginal inserts are formed from resilient material, for example, a mushroom-shaped foam insert (U.S. Pat. No. 4,019,498), an arcuate member with a bladder neck cradle (U.S. Pat. No. 5,036,867) and a folding insert having legs that resiliently urge against the vaginal wall to exert pressure on he urethra (U.S. Pat. No. 5,618,256).

The foregoing apparatus have varying degrees of effectiveness, ease of use, ease of removal, associated discomfort and hygienic impact. Accordingly, it remains an objective in the art to provide a vaginal insert addressing a variety of disorders, such as , urinary incontinence that is maximally effective, comfortable, easy to use and hygienic.

Further, there are numerous conditions of the genital tract, bladder or urinary tract, such as cancer, inflammation, infection or incontinence that may be treated by pharmaceutically active compounds. Many of these compounds are presently orally administered, however, this is a disadvantage in that systemic delivery is used to treat a condition or disease this is possibly more effectively treated by local applications. Also, may of the drugs used for the treatment of urge incontinence are anti-cholinergics with potent side effects. An intravesical administration would accomplish a high concentration of the drug locally without producing a high serum concentration.

Accordingly, it would be desirable to provide a sustained or controlled drug delivery device that is capable of delivery of the drug for an extended period of time, preferably one week or longer. It would be even more desirable to combine a drug delivery device with an apparatus for treating other clinical aliments.

SUMMARY OF THE INVENTION

The problems and disadvantages associated with the conventional techniques and devices utilized as vaginal pessaries are overcome by the present invention which includes a vaginal insert for, among other applications, relieving urinary incontinence. The insert has a generally cylindrical body dimensioned to allow insertion into the vagina. The body has at least one peripheral ring extending from the exterior surface of the body which displaces the vaginal wall, the tissue between the vaginal wall and the urethra to apply support to the vaginal walls and to the urethra assisting in preventing, for example, symptoms of urinary leakage and prolapse.

The vaginal insert is configured to deliver pharmaceutically active compounds such as Oxibutinine, Estradiol, Levonorgestrel and derivatives Lidocaine and similar substances, hormones, prostaglandin and other compounds.

BRIEF DESCRIPTION OF THE FIGURES

For a better understanding of the present invention, reference is made to the following detailed description of an exemplary embodiment considered in conjunction with the accompanying drawings, in which.

DETAILED DESCRIPTION OF THE FIGURES

Figure 1:
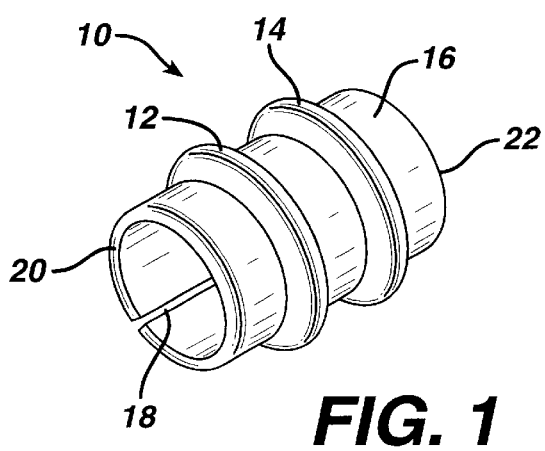
FIG. 1 is a perspective view of a pessary in accordance with an exemplary o embodiment of the present invention.
Figure 2:
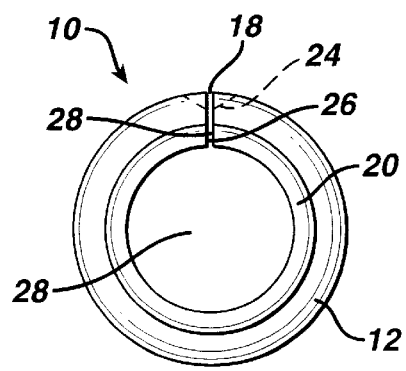
FIG. 2 is a front view of the pessary of FIG. 1.

FIGS. 1 and 2 show a monolithically formed pessary 10 having a generally cylindrical or tubular configuration. A pair of rings 12, 14 extends radially from the peripheral surface 16. Preferably, the pessary 10 also comprises a longitudinal slit 18, which extends along one side from end 20 to end 22. Longitudinal slit 18 permits the pessary 10 to be coiled for insertion and/or use (See FIG. 3). In addition longitudinal slit 18 ensures that, when released after insertion, the pessary 10 supports the vaginal walls properly. The ends 20, 22 and the rings 12, 14 are preferably radiused, i.e., are rounded off, rather than having sharp edges for facilitating insertion into and withdrawal from the vagina and avoiding discomfort to the user during use. The pessary is preferably formed from santoprene or silicon or any other resilient material that is bio-compatible, non-absorptive and resists bacterial growth. Pessary 10 may also incorporate a flexible metal ring incorporated within the flexible material. The flexible metal may be, for example, spring metal that allows the pessary 10 to exert additional pressure against the vaginal walls. Further, the pessary 10 may be loaded, impregnated or surface treated with bacteriacides, deodorants or lubricants. In addition, the pessary 10 may be loaded with various pharmacological compounds, such as hormones and/or Oxibutinine, Estradiol, Levonorgestrel and derivatives Lidocaine and similar substances. Methods of associating drugs, hormones or other pharmacological compounds is well known to those skilled in the art, as for example, described in U.S. Pat. No. 5,188,835 and German Pat. No. 198 29 713, both incorporated in their entirety by reference herein. In still a further embodiment topical medications, ointments or creams could be absorbed into the pessary 10 and slowly released, within a day or two, into the vaginal cavity. This may be for treating dryness or irritation or some other local condition. The ointment could be replenished into the pessary on a infrequent basis as needed. This could be done by infusion (injection), coating or absorption (sponge) of the medication into the device.

It is preferable that the junction of surfaces, e.g., the junction of the rings 12, 14 with the surface 16, be smooth to aid in cleaning and disinfecting the pessary for reuse. It can be expected that the pessary will stay in place for up to three months. The pessary 10 is configured to be easily removable by the user so that it can be cleansed on a weekly basis using a saline solution or other kNown hygienic cleaner. In FIG. 2, a relief groove 24 is depicted in dotted lines to avoid the user's vaginal wall from being pinched between the free ends 26, 28 proximate the slit 18. The pessary has a lumen 28 that may be used to grasp the pessary for removal and which allows the vaginal passage to remain open thereby permitting the Normal flow of menstrual fluids and the continued use of tampons and other sanitary products.

Figure 3:
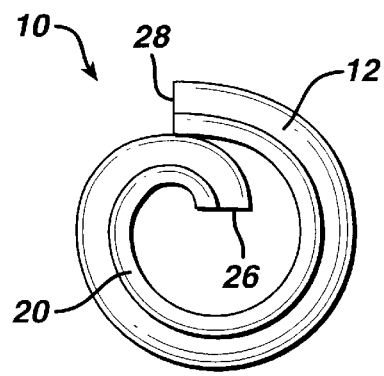
FIG. 3 is a front view of the pessary of FIGS. 1 and 2 in a coiled position.

FIG. 3 shows that the pessary 10 can be coiled to reduce its effective diameter to aid in inserting it into the vagina. In addition, the coiled configuration of the pessary can be utilized as a method of achieving an outwardly directed force that presses the rings 12, 14 against the vaginal walls to achieve the intended effect on the urethra, i.e., to prevent incontinence, or treating various forms of prolapse. In addition, continuous contact between the pessary 10 and the vaginal walls facilitates a controlled release of drugs from the pessary 10 into surrounding tissue. Further, the size of the pessary can be selected relative to the patient's vaginal dimensions such that the pessary is coiled to the desired degree and therefore exerts a selected continuous outward pressure. Since the coiled pessary 10 acts as a spring, it permits contraction and expansion responsive to varying pressure exerted by the vaginal wall due to exercise, coughing, etc. In case of the latter, the pessary exerts a relatively constant pressure on the urethra thereby avoiding incontinence. In the alternative, the pessary can be used in a manner that permits its complete uncoiling, such that the free ends 26, 28 abut one another, as shown in FIG. 2, preventing recoiling or collapse of the pessary under the influence of the user's vaginal musculature.

With respect to sizing of the pessary 10, it is preferable that a variety of sizes be available to suit the individual requirements of the patient. Different sizes of the pessary 10 takes into consideration that each patient has different vaginal dimensions and different requirements in terms of the pressure that the pessary 10 exerts in order to achieve the objectives mentioned throughout. It is intended that the present invention be available in a number of sizes, e.g., from about 20 mm to about 60 mm O.D. at surface 16, a length from about 30 mm to about 50 mm from end 20 to end 22, rings 12, 14 having a width of about 2 mm to about 5 mm and a height above surface 16 of about 2 mm to about 5 mm and having a spacing therebetween of approximately 15 mm.

Figure 4:
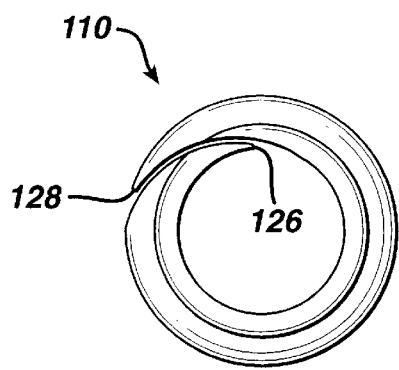
FIG. 4 is a front view of an alternative embodiment of the present invention.

FIG. 4 illustrates an alternative embodiment 110 of the present invention that has features particularly suitable for a coiled pessary 110. Namely, one or both of the free ends 126, 128 are tapered to allow the coiled pessary 110 to have a smooth outer periphery and avoid the abrupt ledge that would otherwise accompany a coiled configuration (as shown in FIG. 3). As Noted above, it is preferable for all edges to be radiused (rounded) to avoid any irritation to the vaginal lining and to promote comfortable use.

Figure 5:
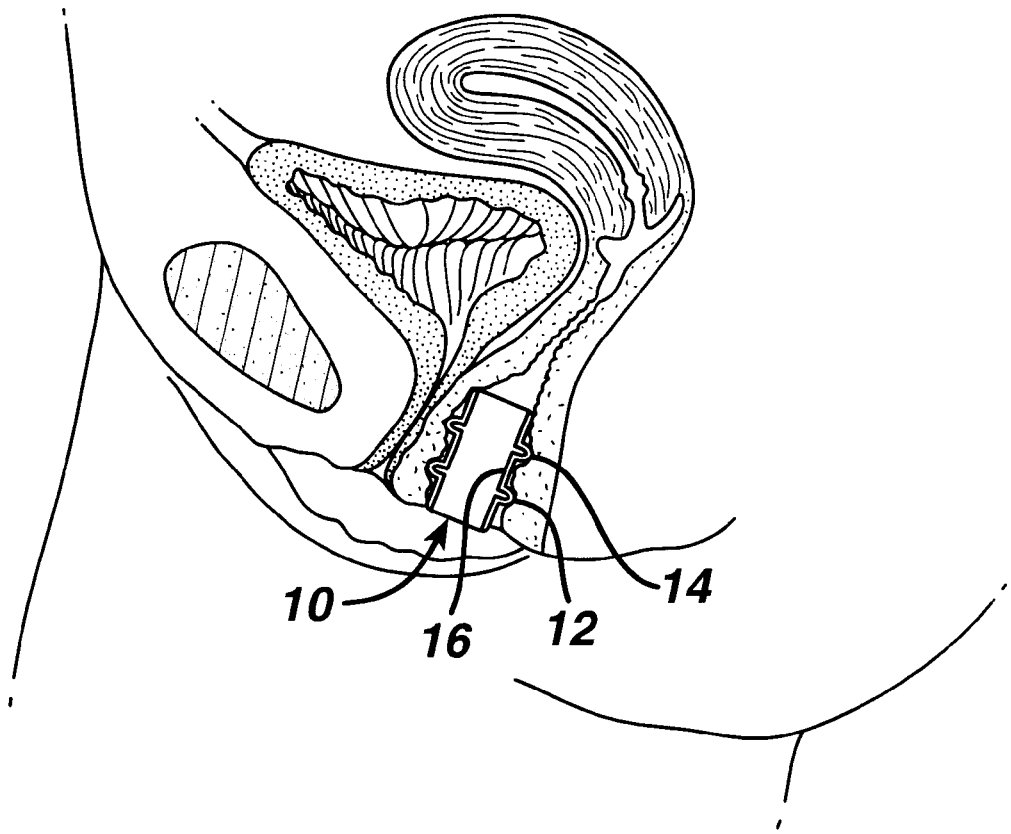
FIG. 5 is a diagrammatic cross-sectional view of the female urogenital system showing a pessary in accordance with the present invention in place within the vagina.

FIG. 5 illustrates the pessary 10 in place within the vagina of a user. The diameter of the pessary 10 as delimited by surface 16 is dimensioned to be accepted comfortably within the vagina, without exerting significant force on the vaginal walls. A greater, localized force is exerted by the rings 12, 14. The rings 12, 14 press into the vaginal wall causing the wall to assume a complementary shape and prevent the pessary from sliding axially once placed within the vagina. The displacement of the vaginal wall by the rings 12, 14 displaces adjacent tissue thereby providing the effects previously mentioned and known to ones skilled in the art. In certain patients, the effect required to treat urinary incontinence necessitates removal of the pessary 10 to allow micturition. The elongated, generally cylindrical configuration of the pessary 10 keeps it oriented axially relative to the axis of the vagina and is comfortable to use due to its complementary shape relative to the vagina and due to the fact that the displacement of the vaginal wall by the pessary is distributed over a large surface area. The fact that the pessary 10 has two rings 12, 14 permits the pessary 10 to work over a greater range of positions, i.e, placement position is Not as critical as it would be if only one ring were present. Because the pessary 10 is symmetrical, it can be inserted with either end first and it does not matter what rotational orientation is used.

As would be appreciated by one skilled in the art, the present invention may also be used as a diagnostic tool. That is, a patient can be easily assessed whether her incontinence may be treated by providing support below the urethra. The pessary 10 is an inexpensive, Non-invasive diagnostic device that provides the surgeon and patient with treatment options without having to perform a surgical procedure. The present invention can therefore be utilized to determine if the patient would be helped by a surgical implant that supports the urethra, such as TVT surgical tape sold by Gynecare, a business unit of Ethicon, Inc., Somerville, N.J.

It should be understood that the embodiments described herein are merely exemplary and that a person skilled in the art may make many variations and modifications without departing from the spirit and scope of the invention as defined in the appended claims. Accordingly, all such variations and modifications are intended to be included within the scope of the invention as defined in the appended claims.

We claim:

1. A vaginal insert for treating various defects, comprising:
a generally cylindrical body adapted to fit within the vagina and adapted to exert pressure on the vaginal walls when inserted therein, said body having a first end and a second end, and a first peripheral ring extending outwardly from the exterior surface of said body at a location intermediate of said first and second ends, said first peripheral ring applying pressure to the vaginal walls in excess of that exerted by the cylindrical body to thereby exert pressure on the urethra to assist in treating pelvic floor defects.

2. The insert of claim 1, wherein said body has a lumen extending therethrough from said first end to said second end of said body.

3. The insert of claim 2, further including a second peripheral ring extending from the exterior surface of the body and disposed on said body intermediate said first peripheral ring and one of said first end and said second end, said first and second peripheral rings having a spacing therebetween, wherein said second peripheral ring applies pressure to the vaginal walls in excess of that exerted by the cylindrical body.

4. The insert of claim 3, wherein said body has a split extending from said first end to said second end and said body further comprises a flexible material permitting said body to be coiled to reduce the outer diameter of said body when said body is coiled.

5. The insert of claim 4, wherein said body uncoils when in place within the vagina, a first free end and a second free end of said body abutting each other at said split.

6. The insert of claim 5, wherein at least one of said first free end and said second free end has a chamfered outer edge to prevent said body from pinching the vagina.

7. The insert of claim 4, wherein said body remains coiled when in place within the vagina, a first free end overlapping a second free end.

8. The insert of claim 7, wherein at least one of said first free end and said second free end are tapered.

9. The insert of claim 3, wherein said body has a length exceeding its diameter.

10. The insert of claim 3, wherein all edges of said body and said first and second peripheral rings are rounded.

11. The insert of claim 2, wherein said insert is a single integral unit.

12. The insert of claim 1, wherein said insert comprises pharmacological compounds.

13. A method for treating various pelvic floor defects, comprising the steps of:

providing a pessary having a generally cylindrical body and a first end and a second end, and having a peripheral ring extending outwardly from an exterior surface of said generally cylindrical body at a location intermediate of said first and second ends;

inserting said pessary in the vagina, such that said cylindrical body exerts pressure on vaginal walls of the vagina and the peripheral ring exerts pressure on the vaginal walls in excess of the pressure exerted by the cylindrical body.

14. The method of claim 13, wherein said pessary has a longitudinal split and a central lumen permitting said pessary to be coiled upon itself, and further including the step of coiling the pessary prior to said step of inserting to reduce the diameter of the pessary.

15. The method of claim 14, further including the step of permitting the pessary to uncoil after said step of insertion.

16. A method for treating various disease states within the urogenital tract, comprising the steps of:

providing a pessary having a generally cylindrical shape and having a prominence extending outwardly from the surface of said generally cylindrical shape, said pessary further comprising pharmacological compounds and having a longitudinal split and a central lumen permitting the pessary to be coiled upon itself;

inserting said pessary in the vagina, such that said prominence exerts pressure on the vaginal walls; and coiling the pessary prior to said step of inserting to reduce the diameter of the pessary.

17. The method of claim 16, further including the step of permitting the pessary to uncoil after said step of insertion.

18. A vaginal insert for treating various defects, comprising:

a generally cylindrical body dimensioned to allow insertion into the vagina, said body having a first end and a second end, and a first peripheral ring extending outwardly from the exterior surface of said body at a location intermediate of said first and second ends, said first peripheral ring applying pressure to the vaginal walls, and the tissue between the vaginal wall and the urethra to apply pressure to the urethra to assist in treating pelvic floor defects, wherein said body has a split extending from said first end to said second end and said body further comprises a flexible material permitting said body to be coiled to reduce the outer diameter of said body when said body is coiled.

19. The insert of claim 18, wherein said body uncoils when in place within the vagina, a first free end and a second free end of said body abutting each other at said split.

20. The insert of claim 19, wherein at least one of said first free end and said second free end has a chamfered outer edge to prevent said body from pinching the vagina.

21. The insert of claim 20, wherein said body remains coiled when in place within the vagina, a first free end overlapping a second free end.

22. The insert of claim 21, wherein at least one of said first free end and said second free end are tapered.

23. The insert according to claim 18, further including a second peripheral ring extending from the exterior surface of the body and disposed on said body intermediate said first peripheral ring and one of said first end and said second end, said first and second.

* * * * *

UNITED STATES PATENT AND TRADEMARK OFFICE
CERTIFICATE OF CORRECTION

PATENT NO. : 6,503,190 B1 Page 1 of 1
DATED : January 7, 2003
INVENTOR(S) : Ulf Ivar Ulmsten and Christer Sjorgren It is certified that error appears in the above-identified patent and that said Letters Patent is hereby corrected as shown below:

<u>Title page,</u>
Item [73], Assignee, should read as follows:
-- [73]  Assignee: Ethicon, Inc. Somerville, NJ (US) --.

Signed and Sealed this

Thirtieth Day of March, 2004

JON W. DUDAS
*Acting Director of the United States Patent and Trademark Office*